United States Patent [19]

Ripka et al.

[11] Patent Number: 4,859,697
[45] Date of Patent: Aug. 22, 1989

[54] SUBSTITUTED ACENAPHTHENES AND THEIR USE AS INHIBITORS OF PHOSPHOLIPASE A2

[75] Inventors: William C. Ripka, Wilmington, Del.; William J. Sipio, Lindenwold, N.J.

[73] Assignee: E. I. Du Pont de Nemours and Company, Wilmington, Del.

[21] Appl. No.: 254,182

[22] Filed: Oct. 6, 1988

Related U.S. Application Data

[62] Division of Ser. No. 860,428, May 17, 1986, Pat. No. 4,806,671.

[51] Int. Cl.$^4$ .................. A61K 31/12; A61K 31/15; A61K 31/18; A61K 31/24; A61K 31/38; A61K 31/135; A61K 31/165; A61K 31/235; A61K 31/275
[52] U.S. Cl. .................... 514/438; 514/448; 514/519; 514/532; 514/534; 514/602; 514/617; 514/618; 514/619; 514/640; 514/656; 514/675; 514/680
[58] Field of Search .............. 514/675, 438, 448, 519, 514/532, 534, 607, 617, 618, 619, 640, 656, 680

Primary Examiner—Stanley J. Friedman

[57] ABSTRACT

Substituted acenaphthenes and their use as inhibitors of phospholipase $A_2$ are provided. The acenaphthenes have the formula

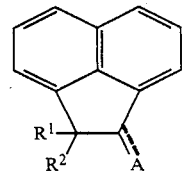

wherein
$R^1$ is H or alkyl;
$R^2$ is alkyl, cycloalkyl, or aryl; and
$R^1$ and $R^2$ taken together are various aryl groups optionally substituted; and
A is =O, =CH$_2$ and derivatives thereof,

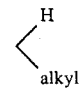

and derivatives thereof, or =NOH and derivatives thereof.

20 Claims, No Drawings

SUBSTITUTED ACENAPHTHENES AND THEIR USE AS INHIBITORS OF PHOSPHOLIPASE A2

This is a division of application Ser. No. 06/860,428, filed May 7, 1986 now U.S. Pat. No. 4,806,671.

BACKGROUND OF THE INVENTION

This invention relates to substituted acenaphthenes, and processes for their preparation, pharmaceutical compositions containing them and pharmaceutical methods using them. These compounds have shown activity as inhibitors of the enzyme phospholipase $A_2$.

The important role of phospholipase $A_2$ in the biosynthesis of prostaglandins and leukotrienes indicates that inhibitors of phospholipase $A_2$ may be valuable therapeutic agents having wide applicability in inflammatory and/or allergic conditions in mammals. Although some currently-available anti-inflammatory agents show activity against phospholipase $A_2$ or other enzymes of the "arachidonic acid cascade," there is a continuing need for safer and more effective drugs capable of treating inflammatory and/or allergic diseases.

W. R. N. Williamson in U.S. Pat. No. 4,246,281 issued Jan. 20, 1981 discloses acenaphthenes of the formula:

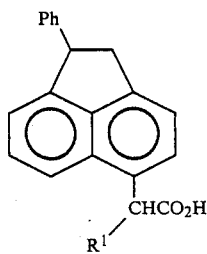

where Ph represents phenyl optionally substituted by halogen and $R^1$ represents hydrogen or $C_1$–$C_4$ alkyl. These compounds are useful anti-inflammatory agents.

S. D. Levine in U.S. Pat. No. 3,755,442, issued Aug. 28, 1973, discloses anti-inflammatory acenaphthyl amides and amines having the formula:

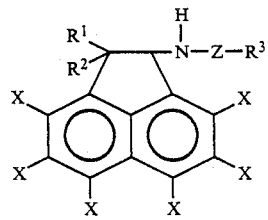

where $R^1$ and $R^2$ may each be hydrogen or a straight or branched chain alkyl radical of up to 6 carbon atoms provided that one $R^1$ and $R^2$ is other than hydrogen. Z may be >C=O or —$CH_2$— and X may be H, halogen, or an alkyl, alkoxy, haloalkyl or haloalkoxy radical of up to 6 carbon atoms.

S. D. Levine and I. T. Harper in U.S. Pat. No. 3,732,299 issued May 8, 1973 disclose anti-inflammatory acenaphthenes of the formula:

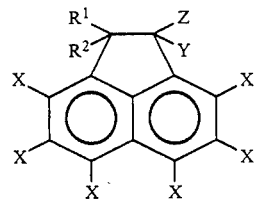

where at least one of $R^1$ and $R^2$ is alkyl and the other may be hydrogen; Z is —CN, —$COOR^3$ (where $R^3$ is hydrogen or a hydrocarbon radical or halophenyl), —$CH_2OH$,

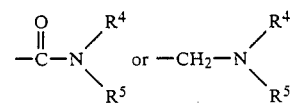

and Y is hydrogen or

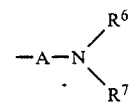

where $R^4$ to $R^7$ are hydrogen or a hydrocarbon radical, A is alkylene, and X is hydrogen, halogen, alkyl, alkoxy, haloalkyl or haloalkoxy.

S. D. Levine in U.S. Pat. No. 3,679,747, issued July 25, 1972, discloses anti-inflammatory acenaphthene derivatives of the formula:

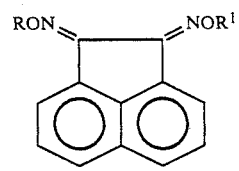

where R and $R^1$ can be the same or different and are $C_1$–$C_3$ alkyl.

C. F. Huebner in U.S. Pat. No. 3,291,830 discloses acenaphthenes of the formula:

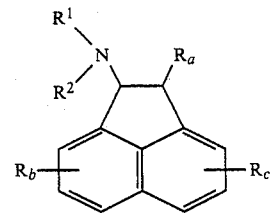

in which $R^1$ is a lower 2-alkynyl radical having preferably from 3–5 carbon atoms, $R^2$ is lower alkyl, the group $R_a$ is a member selected from the group consisting of hydrogen and lower alkyl, and each of the groups $R_b$ and $R_c$ is hydrogen, lower alkyl or halogeno. These compounds are stimulatory agents useful in the treatment of fatigue.

J. F. Kerwin and G. E. Ullyot in U.S. Pat. No. 2,569,814, issued Oct. 2, 1951, disclose acenaphthenes of the formula:

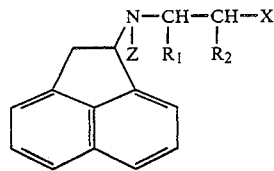

in which Z is a member of the group consisting of lower alkyl groups, lower alkenyl groups, phenylalkyl groups, the alkyl portion of which does not exceed 4 carbon atoms, and methoxy-substituted phenylalkyl groups, the alkyl portion of which does not exceed four carbon atoms; $R_1$ and $R_2$ are hydrogen or methyl groups; X is chlorine or bromine. These compounds have adrenolytic or sympatholytic properties.

SUMMARY OF THE INVENTION

According to the present invention there is provided pharmaceutical compositions containing substituted acenaphthenes of Formula (I) and pharmaceutical methods for using them.

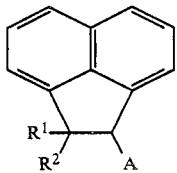

(I)

wherein $R^1$ is H or $C_1$-$C_3$ alkyl;

$R^2$ is $C_3$-$C_{10}$ alkyl, $C_4$-$C_{10}$ cycloalkyl, or aryl($CH_2$)$_n$-; and $R^1$ and $R^2$, taken together, may be aryl—CH=; where n=1-4, and aryl is

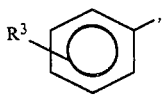

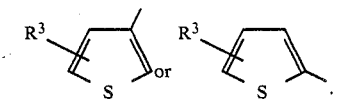

$R^3$ is H, CN, $NO_2$, CO phenyl, $S(O)_eR^5$, halogen, $NHCOR^4$, $CO_2R^4$, $OR^4$, $SO_2N(R^4)_2$, or $NR^6R^7$, wherein e=0, 1 or 2;

$R^4$ is H, $C_1$-$C_6$ alkyl, or phenyl;

$R^5$ is $C_1$-$C_6$ alkyl, phenyl;

$R^6$ and $R^7$, independently are H or $C_1$-$C_4$ alkyl, or, taken together, are $(CH_2)_f$, where f=3-6;

and wherein

A is =O, =CHR$^8$,

=NOR$^8$ $R^8$ is H, $C_1$-$C_6$ alkyl, or $(CH_2)_mW$;

$R^9$ is $C_1$-$C_6$ alkyl, $(CH_2)_mW$, or —$X(CH_2)_mW$;

where m=1-6, X is O,S,

W is —OR$^{10}$, —COR$^{10}$, —OCOR$^{10}$, —OCOOR$^{10}$, NR$^{11}$R$^{12}$, or CONR$^{11}$R$^{12}$;

$R^{10}$ is $C_1$-$C_6$ alkyl;

$R^{11}$, $R^{12}$, independently are H, $C_1$-$C_6$ alkyl or taken together, are $(CH_2)_g$, where g=3-6;

with the following provisos:

1. When A=O then $R^1$ and $R^2$ taken together are not 4-$(CH_3)_2NC_6H_4CH=$, 2-MeOC$_6$H$_4$CH=3-MeOC$_6$H$_4$CH=, 4-FC$_6$H$_4$CH=, or 4-MeOC$_6$H$_4$CH=.
2. When A is =NOR$_8$, R$_8$ is not H.
3. When $R^8$ is hydrogen, then $R^2$ is not $C_3$-$C_{10}$ alkyl or $C_4$-$C_{10}$ cycloalkyl.
4. When $R^2$ is 4-FC$_6$H$_4$CH$_2$—, 3-CH$_3$CONHC$_6$H$_4$CH$_2$—, or 4-NO$_2$C$_6$H$_4$CH$_2$—, then A is not =CH$_2$.
5. When A=O, then $R^2$ is not $C_3$-$C_{10}$ alkyl or $C_4$-$C_{10}$ cycloalkyl.
6. When A is CH$_2$NR$^{11}$R$^{12}$, then $R^2$ is not alkyl.

Pharmaceutical compositions preferred for their phospholipase $A_2$ inhibitory activity contain a compound of Formula (I) where:

A is =O, =CHR$^8$,

or

W is NR$^{11}$R$^{12}$, CONR$^{11}$R$^{12}$.

More preferred are those where:

$R^1$ is H or CH$_3$; or $R^2$ is aryl-(CH$_2$)n; or $R^1$ and $R^2$, taken together, are aryl—CH=; where n=1-2; or $R^3$ is halogen, CN, OCH$_3$, OR$^4$, or NR$^6$R$^7$; or A is =O, =CHR$^8$, or

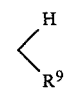

(provided that if A is

then $R^9$ is trans to $R^2$), where m=1-3; or

W is NR$^{11}$R$^{12}$ or COR$^{11}$R$^{12}$.

Specifically preferred for their phospholipase $A_2$ inhibitory activity are:

a. 1,2-Dihydro-1-[(3-methoxyphenyl)methyl)]-1-methyl-2-methylene acenaphthene
b. 3-[(1,2-Dihydro-1-methyl-2-methylene-1-acenaphthenyl)-methyl]phenol
c. 3-(1,2-Dihydro-2-[(3-methoxyphenyl)methyl]-2-methyl-1-acenaphthenylidene)propanamine
d. 2-[(3-Fluorophenyl)methylene]-1(2H)-acenaphthylenone
e. 1,2-Dihydro-1-[(3-cyanophenyl)methyl)]-1-methyl-2-methylene acenaphthene.

Also provided in the invention are novel substituted acenaphthenes within Formula (I) which are defined by Formula (II).

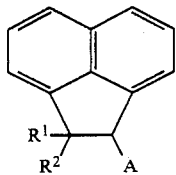
(II)

wherein
$R^1$ is H or $C_1$-$C_3$ alkyl;
$R^2$ is $C_3$-$C_{10}$ alkyl, $C_4$-$C_{10}$ cycloalkyl, or aryl$(CH_2)_n$; and
$R^1$ and $R^2$, taken together, may be aryl—CH=; where n=1-4, and
aryl is

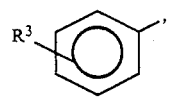,

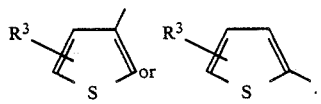

$R^3$ is H, CN, $NO_2$, CO-phenyl, $S(O)_eR^5$, halogen, $NHCOR^4$, $CO_2R^4$, $OR^4$, $SO_2N(R^4)_2$, or $NR^6R^7$, wherein e=0, 1 or 2;
$R^4$ is H, $C_1$-$C_6$ alkyl, or phenyl;
$R^5$ is $C_1$-$C_6$ alkyl, phenyl;
$R^6$ and $R^7$, independently are H or $C_1$-$C_4$ alkyl, or, taken together, are $(CH_2)_f$, where f=3-6;
and wherein
A is =O, =CHR$^8$,

=NOR$^8$
$R^8$ is H, $C_1$-$C_6$ alkyl, or $(CH_2)_mW$;
$R^9$ is $C_1$-$C_6$ alkyl, $(CH_2)_mW$, or —$X(CH_2)_mW$;
where m=1-6, X is O,S,
W is —$OR^{10}$, —$COR^{10}$, —$OCOR^{10}$, —$OCOOR^{10}$, $NR^{11}R^{12}$, or $CONR^{11}R^{12}$;
$R^{10}$ is $C_{1-C_6}$ alkyl;
$R^{11}$, $R^{12}$, independently are H, $C_1$-$C_6$ alkyl or taken together, are $(CH_2)_g$, where g=3-6;
with the following provisos;
1. When A=O, $R^1$ and $R^2$ are not aryl—CH=, and $R^2$ is not $C_3$-$C_{10}$ alkyl.
2. Where A is =NOR$^8$, $R^8$ is not H;
3. When $R^8$ is hydrogen, then $R^2$ is not $C_3$-$C_{10}$ alkyl or $C_4$-$C_{10}$ cycloalkyl;
4. When $R^2$ is 4-$FC_6H_4CH_2$, 3-$CH_3CONHC_6H_4CH_2$, or 4-$NO_2C_6H_4CH_2$, then A is not =$CH_2$;
5. When A is $CH_2NR^{11}R^{12}$, $R^2$ is not alkyl.
Preferred novel compounds of Formula (II) are those where:
A is =O, =CHR$^8$,

or
W is $NR^{11}R^{12}$, $CONR^{11}R^{12}$.
More preferred compounds of formula (II) are those where:
$R^1$ is H or $CH_3$; or
$R^2$ is aryl-$(CH_2)_n$; or
$R^1$ and $R^2$, taken together, are aryl—CH=; where n=1-2, or
$R^3$ is halogen, CN, $OCH_3$, $OR^4$, or $NR^6R^7$; or
A is =O, =CHR$^8$, or

(provided that if A is

then $R^9$ is trans to $R^2$),
where m=1-3; or
W is $NR^{11}R^{12}$ or $COR^{11}R^{12}$.
Specifically preferred novel compounds are the same ones preferred for their phospholipase $A_2$ inhibitory activity except compound d.

DETAILED DESCRIPTION OF THE INVENTION

The compounds of this invention have demonstrated pharmacological activity as inhibitors of the enzyme phospholipase $A_2$ ($PLA_2$). Phospholipase $A_2$ acts to release arachidonic acid from phospholipids. Once released, arachidonic acid is rapidly metabolized by a variety of enzymes of the "arachidonic acid cascade." The products of the arachidonic acid cascade include prostaglandins, leukotrienes, and related compounds. These compounds exhibit a remarkably broad spectrum of biological activity, and inhibition of their biosynthesis is recognized as a valuable mechanism for production of anti-inflammatory effects.

Both prostaglandins and leukotrienes are believed to have important functions as mediators of inflammation and currently available drugs which inhibit their production are of significant therapeutic value in man and other mammals. Nonsteroidal anti-inflammatory agents such as the salicylates act as inhibitors of prostaglandin synthesis from arachidonic acid by inhibiting the cyclooxygenases. This inhibition of prostaglandin synthesis is believed to be the basis for many of the therapeutic effects of the aspirin-like drugs. The anti-inflammatory activity of the glucocorticoids, on the other hand, is believed to be at least partly due to their ability to induce the biosynthesis of a phospholipase $A_2$ inhibitor, thereby diminishing the release of arachidonic acid from phospholipids. By decreasing concentrations of arachidonic acid, the substrate for the entire arachidonic acid cascade, production of leukotrienes as well as prostaglandins can be decreased.

Many diseases and conditions in man and other mammals have inflammatory and/or allergic components, e.g., rheumatoid arthritis and other rheumatic disorders, various collagen diseases, dermatoses, psoriasis, hypersensitivity and immune reactions, bronchospastic diseases such as asthma, and disorders of platelet aggregation. Because the compounds of this invention have shown activity as $PLA_2$ inhibitors, valuable pharmacological activity in these and other diseases or conditions mediated by the various products of the arachidonic acid cascade is to be expected.

a catalyst such as palladium on carbon. Alkylation of the intermediate ketone with an alkyl halide under standard conditions described in the chemical literature yield the ketones (VII). The required aldehydes (V) are either available commercially, or may be prepared using techniques and methods reported in the chemical literature (Scheme 1).

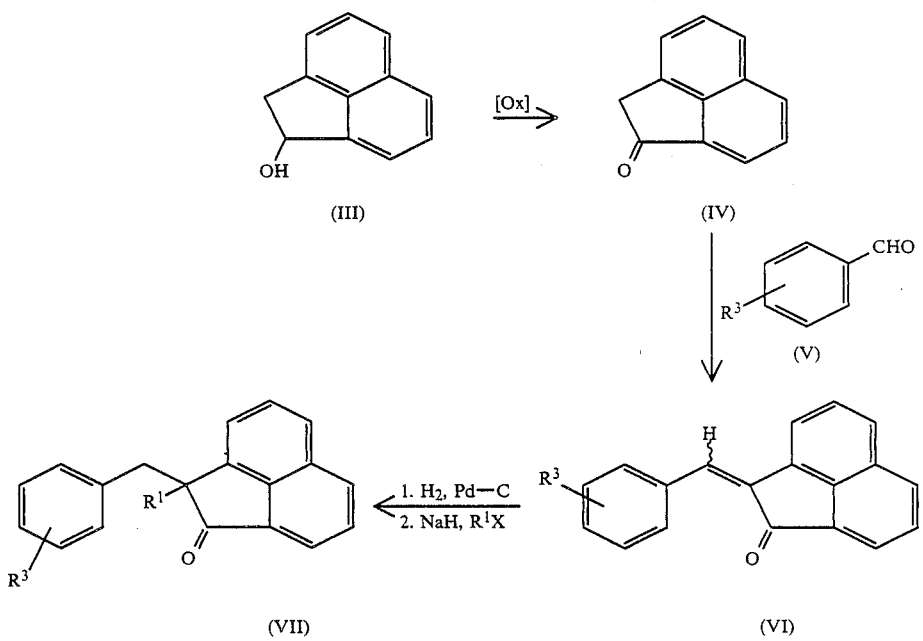

Scheme 1

Synthesis

The novel compounds of Formula II may be prepared using the reactions and techniques described in this section. The reactions are usually performed in a solvent appropriate to the reagents and materials employed, and suitable for the transformation being effected. Unless stated otherwise, the reactions are performed at temperatures between $-78°$ C. and the boiling point of the solvent used, as appropriate for a reasonable rate of reaction and the stability of the reagents, solvents and products involved. In some cases, functional groups on the starting materials may need to be protected by standard protecting groups reported in the chemical literature. Such protecting groups include methyl ethers to protect hydroxyl groups, ethylene ketals to protect ketones, and acetals to protect aldehydes.

Compounds of Formula (VII), where $R^3$ is H, CN, OMe, Halogen, and $R^1$ is H or $C_1$–$C_3$ alkyl, may be prepared via the oxidation of the alcohol (III) with a chromium salt to yield ketones (IV). An example of this technique is reported by E. J. Corey et al., *Tetrahedron Letters*, 2467 (1975). Aldol condensation of ketone (IV) with the appropriately substituted aldehyde (V) under basic conditions yields the benzylidene ketone (VI). An example of this conversion is described by O. Tsuge et al., *Bulletin of the Chemical Society of Japan*, 42, 181–185 (1969). Catalytic reduction of the multiple bond in ketone (VI) is performed with hydrogen in the presence of Alternatively, compounds of the formula (VII), where $R^3$ is $NO_2$, aryl is benzyl, and $R^1$ is H or $C_1$–$C_3$ alkyl may be prepared via alkylation of the substituted acenaphthenone (VIII) with the appropriate alkyl or aryl halide under standard conditions described in the chemical literature. The preparation of the acenaphthenone (VIII) and its alkylation with alkyl or aryl halides is described by S. Levine in U.S. Pat. No. 3,755,422 (Scheme 2).

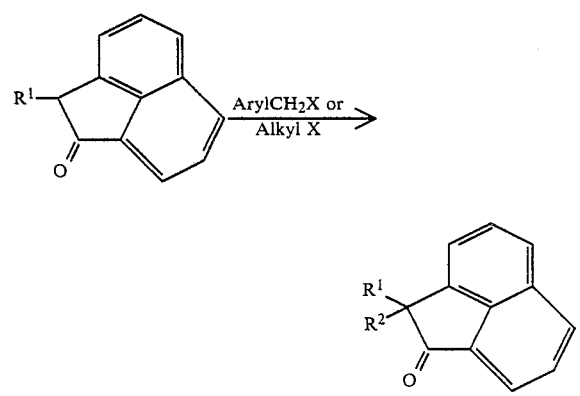

Scheme 2

Also compounds of the formula (VII) where $R^3$ is OH and $R^1$ is H or $C_1$–$C_3$ alkyl may be prepared via demethylation of the methyl ether in (IX) using boron tribromide (Scheme 3) under standard conditions described in the chemical literature. Compounds of the formula (IX) are prepared via the methods described in Scheme 1.

Scheme 3

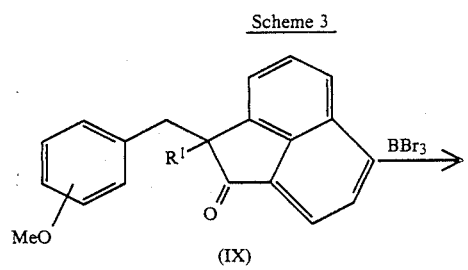

(IX)

(VII)

Compounds of the formula (XI), where $R^1$ and $R^2$ are as described above, can be prepared by two methods. Alcohols of the formula (X) may be prepared by treatment of ketone (VII) with an organometallic reagent such as an alkyllithium or alkylmagnesium halide. This method is limited to compounds where $R^3$ is not CN, CO-phenyl, $CO_2R^4$, or $NHCOR^4$, where $R^4$ is as described previously. Olefins of the formula (XI) may be prepared from alcohols (X) by dehydration using any of a variety of techniques commonly reported in the chemical literature. Alternatively, the olefins of formula (XI) may be prepared by treatment of the ketones (VII) with a reagent such as an alkylidene triarylphosphorane (XII) (the Wittig reaction). When $R^8$ is not H, the Z or the E isomer or a mixture of the two, may be obtained from these reactions (Scheme 4).

Scheme 4

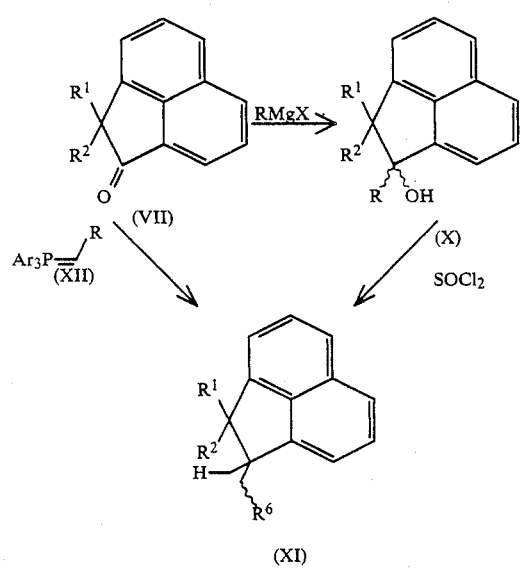

Compounds of the formula (XIII), where $R^1$, $R^2$, and $R^8$ are as described above. Catalytic reduction of the multiple bond in olefin (XI) is performed with hydrogen in the presence of a catalyst such as palladium on carbon. This method is limited to compounds in which $R^3$ is not $NO_2$ (Scheme 5).

Scheme 5

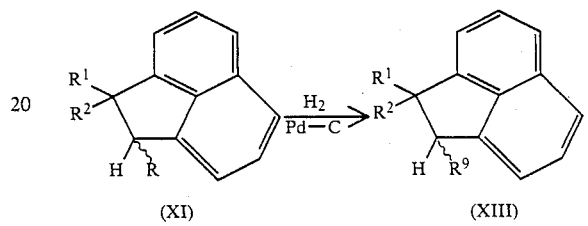

(XI)                              (XIII)

Compounds of the formula (XI) where $R^8$ is $(CH_2)_2NH_2$, may be prepared from ketone (VII) via the addition of an alkylmagnesium halide derived from 2-(2-Bromoethyl)-1,3-dioxane. An example of this method is described by J. C. Stowell, *Journal of Organic Chemistry*, 41, No. 3, 560–561 (1976). Olefins of the formula (XIV) may be prepared from the intermediate alcohol [formed by organometallic addition to ketone (VII)] by dehydration using any of a variety of techniques commonly reported in the chemical literature. Transacetalization of acetal (XIV) to acetal (XV) is achieved in acidic methanol by the method of J. C. Stowell et al., *Synthesis*, 132, (1979). Acetal (XV) is then hydrolyzed via standard methods to yield aldehyde (XVI). Aldehyde (XVI) is then converted to the O-methyl oxime (XVII) via the method described by H. Feuer et al., *Journal of Organic Chemistry*, 34, No. 6, 1817–1821 (1969). O-methyl oxime (XVII) is reduced to the amine (XI) using the reagent, sodium trifluoroacetoxyborohydride, described by N. Umino at al., *Chem. Pharm. Bull.*, 26, 2897–2898, (1978). Amine (XI) may be converted to its hydrochloride salt via methods described in the chemical literature (Scheme 6).

Scheme 6

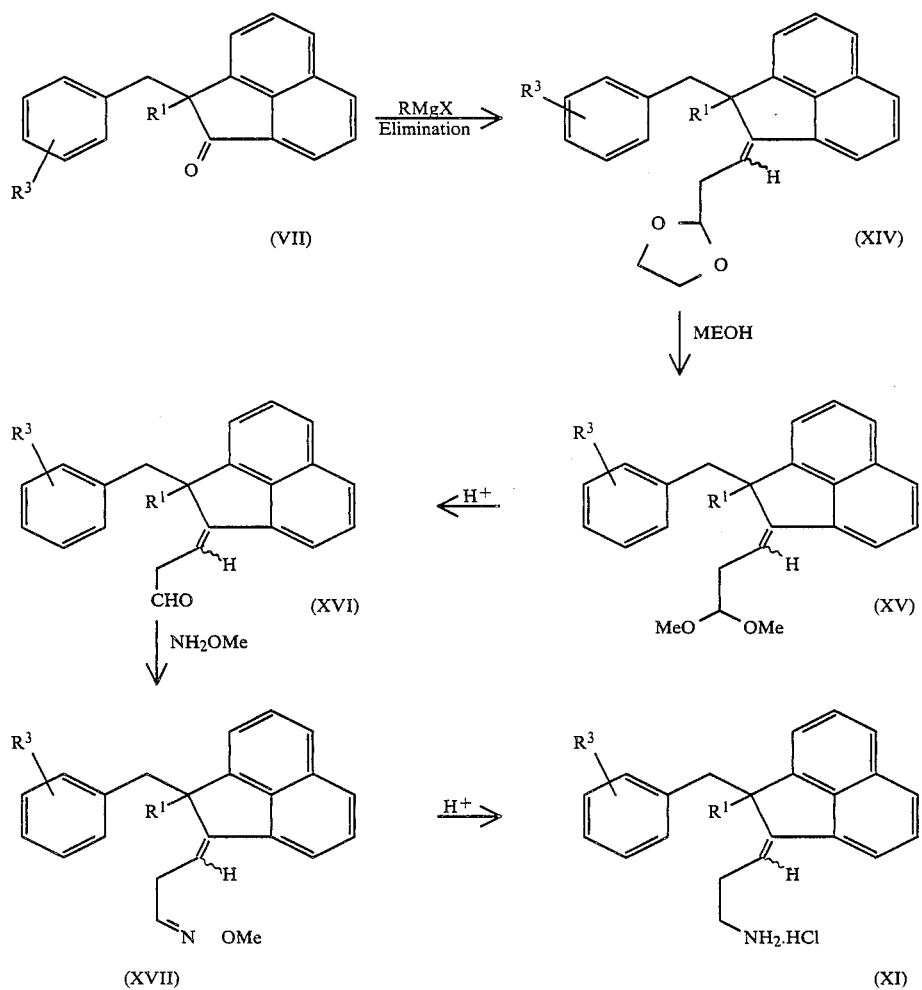

Compounds of the formula (XXIV) where $R^1$ is H, $R^2$ is cyclohexyl, n is 3, and $R^9$ is $O(CH_2)_nNH_2$ and trans to $R^2$ may be prepared frm epoxide (XVIII) via the addition of an alkylmagnesium halide to yield alcohols of the formula (XIX). Epoxide (XVIII) is prepared according to the method of T. Kinstle, *Journal of Organic Chemistry*, 35, No. 1, 257-258 (1970). Compounds of the formula (XX) are prepared via alkylation of alcohol (XIX) with an allyl halide under standard conditions. Alcohols (XXI) are produced via hydroboration. Alcohol (XXI) is oxidized to the aldehyde (XXII) using a chromium salt under standard conditions. Aldehyde (XXII) is converted to the O-methyl oxime under conditions described previously. O-methyl oxime (XXIII) is reduced to the amine (XXIV) under conditions described previously. Amine (XXIV) may be converted to its hydrochloride salt via methods described in the chemical literature (Scheme 7).

Scheme 7

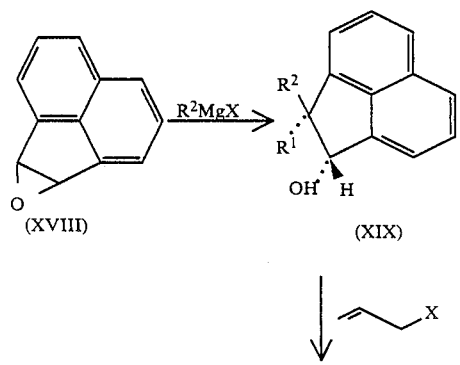

-continued
Scheme 7

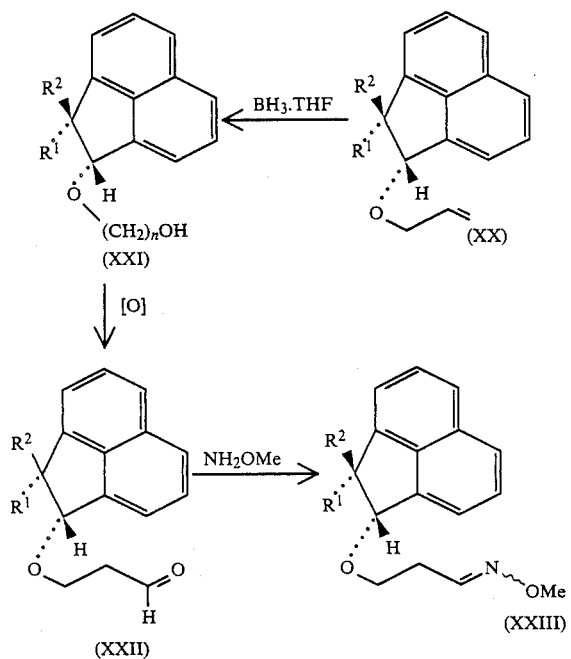

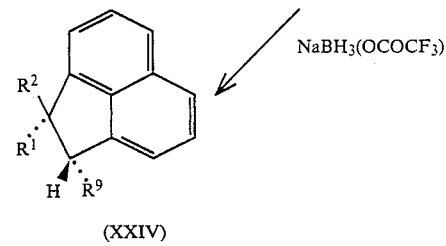

Compounds of the formula (XXIV) where $R^1$ is H, $R^3$ is not $NO_2$, n is 2, $R^9$ is $O(CH_2)_nNH_2$ and trans to $R^2$ may be prepared from the monoketal (XXV). The preparation of monoketal (XXV) is described by A. Merz et al., *Tetrahedron Letters*, 40, 665-671 (1984). Olefins of the formula (XXVI) may be prepared by treatment of monoketal (XXV) with a reagent such as a benzylidene triarylphosphorane (XII) (the Wittig reaction). Catalytic reduction of the multiple bond in (XXVI) is performed with hydrogen in the presence of a catalyst such as palladium on carbon to yield ketal (XXVII). Reductive cleavage of ketal (XXVII) via the method described in *Organic Synthesis*, Collective Vol. V, 303, J. Wiley and Sons (1973) yields alcohol (XXI) as a mixture of cis and trans isomers. Alcohol (XXI) is converted to amine (XXIV) and its hydrochloride salt by the methods previously described (Scheme 8).

Scheme 8

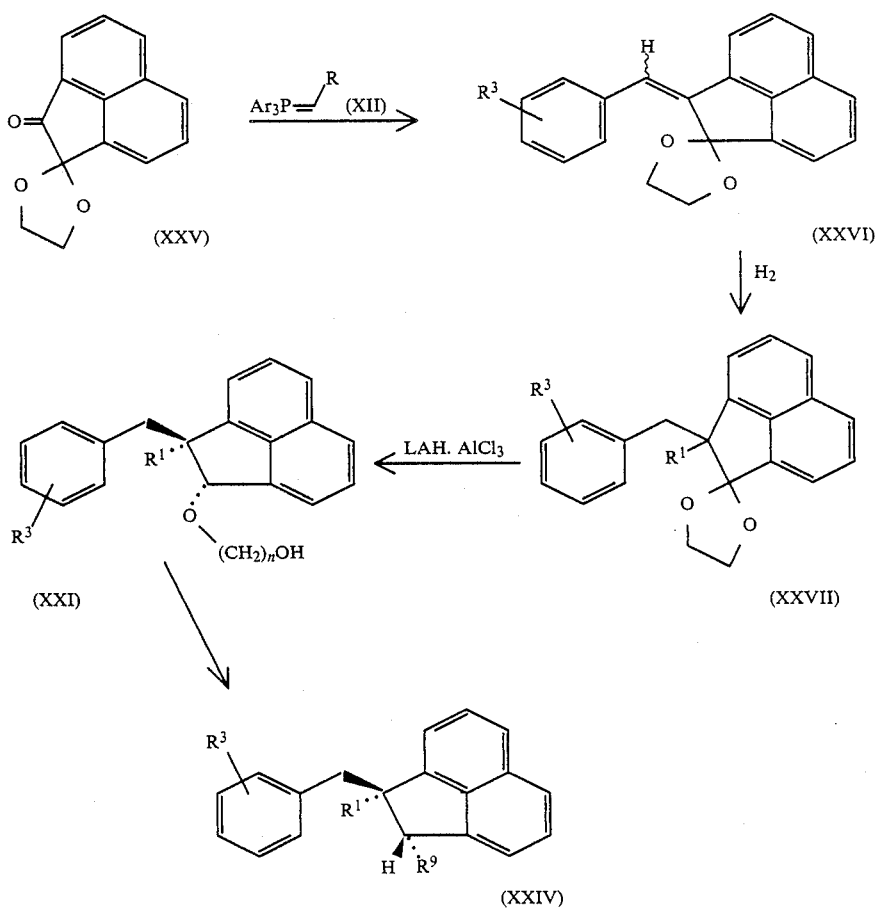

The compounds of this invention and their preparation are illustrated further in the following examples. All temperatures are in degrees Centigrade and parts and percentages by weight. In these Examples, unless otherwise indicated, the reactions were performed under an atmosphere of dry nitrogen; "isolation by extraction" refers to the liquid-liquid extraction of a water containing mixture with an indicated solvent, followed by drying the organic phase over magnesium sulfate, filtering, and evaporation of the solvent under reduced pressure; chromatography refers to the method of medium-pressure column chromatography described by W. C. Still, et al., *Journal of Organic Chemistry*, 43, 2923 (1978).

EXAMPLE 1

Method A

Part A:
2-[((3-Methoxyphenyl)methylene)]-1-(2H)-acenaphthenone,

To a solution of acenaphthenone (1.68 g, 0.01 mole) and m-anisaldehyde (1.63 g, 0.012 mole) in 25 ml of absolute ethanol, 3.0 ml of 1N sodium hydroxide was added dropwise at 25°. The mixture was stirred at room temperature for 20 minutes and then refluxed for 5 minutes. Hydrochloric acid (5.0 ml of a 1N solution) was added to the reaction mixture. Yellow crystals were collected, washed with water and dried. The solid was recrystallized (ethanol) to give the title compound as yellow needles (2.43 g, 85%), m.p. 119°–121°.

Part B: 2-(3-Methoxybenzyl)-1-acenaphthenone

A solution of the product of Part A (7.8 g, 0.027 mole) in ethyl acetate (300 ml) containing 10% palladium on carbon (2.0 g) was placed on a Parr shaker (20 psi., H$_2$) for 1 hr. at room temperature. The reaction mixture was filtered through Celite ® (diatomaceous silica, Johns-Manville Corp.) under nitrogen. The solvent was evaporated and the oil was chromatographed on silica with ethyl acetate/hexane. Recrystallization (ethanol) provided the title compound (7.0 g, 95%) as a white solid, m.p. 81°–83°.

Part C:
2-[((3-methoxyphenyl)-methyl)]-2-methyl-1(2H)-acenaphthenone

A solution of the product of Part B (5.0 g, 0.017 mole) in tetrahydrofuran (30.0 ml) was added dropwise to a solution of sodium hydride (1.83 g, 0.076 mole, 50% oil dispersion) in tetrahydrofuran (70.0 ml) at 0°. The reaction mixture was stirred for 15 minutes. Iodomethane (12.32 g, 0.086 mole) was then added dropwise at 0°. The reaction mixture was stirred at room temperature for 24 hours. It was then poured onto ice and isolated by extraction with diethyl ether. The material was chromatographed on silica with ethyl acetate/hexane. Recrystallization (ethyl acetate/hexane) provided the title compound (4.20 g, 80%) as a white solid, m.p. 65°–67°.

Part D:
1,2-Dihydro-1-[((3-methoxyphenyl)-methyl)]-1-methyl-2-methylene-acenaphthene To a solution of methyltriphenylphosphonium bromide (3.54 g, 0.01 mole) in tetrahydrofuran (20.0 ml) is added potassium tert-butoxide (1.25 g, 0.11 mole) at 0°. The reaction mixture is stirred for 15 minutes. A solution of the product of Part C (1.0 g, 0.003 mole) in tetrahydrofuran (10.0 ml) is added dropwise at 0°. The mixture is stirred for 2 hours, poured into water, and isolated by extraction with diethyl ether. The material was chromatographed on silica with hexane to provide the title compound (0.88 g, 89%) as an oil.

EXAMPLE 2

Method B

Part A:
2-[((3-Hydroxyphenyl)methyl)]-2-methyl-1(2H)-acenaphthenone

A solution of the product of Part C, Example 1 (6.10 g, 0.020 mole) is dissolved in methylene chloride (120.0 ml) at −78°. To this solution is added dropwise boron tribromide (24.0 ml of a 1M solution). The reaction mixture is brought to room temperature and stirred for 1 hour, poured into water, and isolated by extraction with methylene chloride. The material was chromatographed on silica with ethyl acetate/hexane to provide the title compound (0.870 g, 15%) as a tan solid, m.p. 145°–147°.

Part B:
3-[((1,2-Dihydro-1-methyl-2-methylene-1-acenaphthenyl)-methyl)]-phenol

To a solution of methyltriphenylphosphonium bromide (4.40 g, 0.012 mole) in tetrahydrofuran (90.0 ml) is added potassium tert-butoxide (2.11 g, 0.018 mole) at 0°. The reaction mixture is stirred at 0° for 30 minutes. A solution of the product of Part A (0.880 g, 0.003 mole) in tetrahydrofuran (45.0 ml) is added dropwise at 0°. The mixture is stirred for 2 hours, poured into water, and isolated by extraction with diethyl ether. The material was chromatographed on silica with ethyl acetate/hexane to provide the title compound (0.253 g, 29%) as an oil.

EXAMPLE 3

Method C

Part A: 2-Methyl-2-(3'-cyanobenzyl)-1-acenaphthenone

A solution of 2-methyl-1-acenaphthenone (1.00 g, 0.005 mole) in tetrahydrofuran (20.0 ml) was added dropwise to a solution of sodium hydride (0.580 g, 0.024 mole, 50% oil dispersion) in tetrahydrofuran (35.0 ml) at 0°. The reaction mixture was stirred for 2 hours at room temperature. At 0°, α-Bromo-m-tolunitrile (1.37 g, 0.007 mole) in tetrahydrofuran (10.0 ml) was added dropwise. The mixture was stirred for 24 hours at room temperature, poured into water, and isolated by extraction with diethyl ether. The material was chromatographed on silica with ethylacetate/hexane providing the title compound as an oil (1.55 g, 95%).

Part B:
1,2-dihydro-1-(3'-cyanobenzyl)-1-methyl-2-methylene acenapthene

To a solution of methyltriphenyl phosphonium bromide (3.38 g, 0.0094 mole) in tetrahydrofuran (70.0 ml) is added potassium tert-butoxide (1.16 g, 0.01 mole) at 0°. The reaction mixture is stirred at 0° for 30 minutes. A solution of the product of Part A (1.0 g, 0.03 mole) in tetrahydrofuran (30.0 ml) is added dropwise at 0°. The mixture is stirred for 24 hours at room temperature, poured onto ice, and isolated by extraction with diethyl ether. The material was chromatographed on silica with ethyl acetate/hexane to afford the title compound as a solid (0.745 g, 75%), m.p. 94°–96°.

EXAMPLE 4

Method D

Part A:

1-(Hydroxy)-1-(butyl)-2-methyl-2-[(3-methoxy)benzyl]-acenaphthene

To a solution of the product of Part C, Example 1 (0.500 g, 0.0016 mole) in tetrahydrofuran (20.0 ml) at −78° was added dropwise n-butyllithium (3.0 ml, 1.55 M). The mixture was stirred at room temperature for 24 hours, poured into water, and isolated by extraction with diethyl ether. The mixture was chromatographed on silica with ethyl acetate/hexane providing a mixture of cis and trans isomers as an oil (0.380 g, 64%).

Part B:

2-Methyl-2-(3'-methoxybenzyl)-1-(Z,E)-butenyl-acenaphthene

To a solution of the product of part A (0.380 g, 0.001 mole) in methylene chloride (30.0 ml) was added pyridinium 4-toluenesulfonate (0.200 g, 0.0008 mole) at room temperature. The reaction mixture was stirred for 24 hours, poured into water, and isolated by extraction with methylene chloride. The material was chromatographed with ethylacetate/hexane on silica providing the title compound (0.198 g, 55%) as an oil.

EXAMPLE 5

Part A:

1-[2-(1,3-Dioxane-2-yl)ethyl]-1,2-dihydro-2-](3-methoxyphenyl)-methyl)]-2-methyl-1-acenaphthenol To a solution of 2-(2-bromoethyl)-1,3-dioxane (15.08 g, 0.077 mole) in tetrahydrofuran (65.0 ml) is added magnesium chips (2.50 g, 0.103 mole) at room temperature. The mixture is refluxed for 30 minutes, cooled to room temperature, and added dropwise via syringe to a solution of the product of Part C. Example 1 (5.80 g, 0.020 mole) in tetrahydrofuran (55.0 ml) at −78°. The reaction mixture is stirred at room temperature for 2 hours, poured into saturated ammonium chloride (aqueous), and isolated by extraction with diethylether. The mixture was chromatographed on silica with ethyl acetate/hexane affording a solid (6.10 g, 76%), m.p. 120°–122°.

Part B:

2-[(2-[(1,2-Dihydro-2-(3-methoxyphenyl)methyl)]-2-methyl-1-acenaphthylidene[]-ethyl 1,3-dioxane To a solution of the product of Part A (1.00 g, 0.0024 mole) in pyridine (4.0 ml) at 0° was added thionyl chloride (0.350 g, 0.003 mole). The mixture was stirred at room temperature for 2 hours, poured into water, and isolated by extraction with diethyl ether. The materials was chromatographed on silica with ethyl acetate/hexane to afford an oil (0.425 g, 45%); mass spec. m/z=418.

Part C:

2-Methyl-2-(3'-methoxybenzyl)-1-(Z,E)-but-(4'-dimethylacetal)-enyl-acenaphthene

To a solution of the product of Part B (2.60 g, 0.0065 mole) in methanol (150.0 ml) was added p-toluenesulfonic acid (0.500 g, 0.0026 mole) at room temperature. The reaction mixture was refluxed overnight. The reaction mixture was cooled, poured into saturated sodium bicarbonate (aqueous) and the methanol was removed in vacuo. The residue was isolated by extraction with methylene chloride and chromatographed on silica with ethyl acetate/hexane to afford an oil (1.63 g, 65%); mass spec. m/z=388.

Part D:

2-Methyl-2-(3'-methoxybenzyl)-1-but-(4'-methoximino)-enyl-acenaphthene

The product of Part C (1.50 g, 0.0038 mole) dissolved in 10 ml acetate acid, 2.0 ml H$_2$O, 2.0 ml tetrahydrofuran is heated to 100° for 2 hours. The mixture was cooled, poured into water, and isolated by extraction with ether. Crude aldehyde (1.50 g, 0.0043 mole) was dissolved in ethanol (20.0 ml). To this solution was added methoxyamine hydrochloride (1.00 g, 0.012 mole) at room temperature. The reaction mixture was refluxed for 30 minutes and cooled. The solvent was removed in vacuo, water was added, and the product isolated by extraction with methylene chloride. Purification by chromatography with ethyl acetate/hexane afforded an oil (0.600 g, 37%); mass spec. m/z=371.

Part E:

3-[(1,2-Dihydro-2-[(3-methoxyphenyl)-methyl]-2-methyl-1-acenaphthenylidene)] propanamine hydrochloride Sodium borohydride (0.306 g, 0.008 mole) is dissolved in tetrahydrofuran (15.0 ml) at room temperature. To this solution was added trifluoroacetic acid (0.922 g, 0.008 mole) dropwise at room temperature. The reaction mixture was stirred at room temperature for 30 minutes. To this solution was added the product of Part D (0.600 g, 0.0016 mole) in tetrahydrofuran (5.0 ml) and the mixture was heated at reflux for 1 hour. The reaction mixture was quenched with water and evaporated in vacuo. The residue was extracted with methylene chloride and evaporated. The residue was diluted with ether, hydrochloric acid was bubbled through the solution and the precipitate filtered to yield a white solid (hygroscopic, 0.274 g, 45%); mass spec. m/z=343.

The compounds of Examples 1, 2, 3, 4, and 5 are shown in Table 1, as well as other compounds which were prepared or could be prepared using the procedures of the aforementioned examples.

TABLE 1

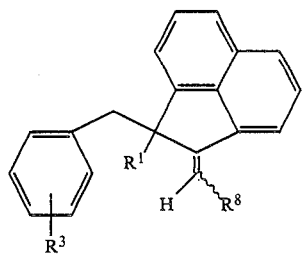

| EX. | R¹ | R³ | R⁸ | METHOD | YIELD % | MP °C. |
|---|---|---|---|---|---|---|
| 1 | CH₃ | 3-OCH₃ | H | A | 89 | (oil)$^a$ |
| 2 | CH₃ | 3-OH | H | B | 29 | (oil)$^b$ |
| 3 | CH₃ | 3-CN | H | C | 75 | 94°–96° |
| 4 | CH₃ | 3-OCH₃ | Pr | D | 55 | (oil)$^c$ |
| 5 | CH₃ | 3-OCH₃ | (CH₃)₂NH₂.HCl | — | 45 | (hygroscopic)$^d$ |
| 6 | CH₃ | 4-OH | H | B | 35 | (oil)$^e$ |
| 7 | CH₃ | 2-OH | H | B | 55 | (oil)$^f$ |
| 8 | CH₃ | 3-F | H | A | 92 | (oil)$^g$ |
| 9 | CH₃ | 3-OCH₃ | CH₃ | A | 34 | (oil)$^h$ |
| 10 | CH₂CH₃ | 3-OCH₃ | H | A | 95 | (oil)$^i$ |
| 11 | CH₃ | 4-F | Pr | A | 25 | (oil)$^j$ |
| 12 | CH₃ | 2-OCH₃ | H | A | 35 | (oil)$^k$ |
| 13 | CH₃ | 4-OCH₃ | H | A | 53 | (oil)$^l$ |
| 14 | CH₃ | H | Pr | A | 18 | (oil)$^m$ |
| 15 | CH₃ | 2-F | H | A | 83 | (oil)$^n$ |
| 16 | CH₃ | H | H | A | 80 | (oil)$^o$ |
| 17 | CH₃ | 4-CN | H | C | 43 | 99–101 |
| 18 | CH₃ | 3-NH₂.HCl | H | C | 88 | 176–179 |
| 19 | CH₃ | 4-NH₂ | H | C | 88 | (oil)$^p$ |
| 20 | CH₃ | 3-NH₂ | H | C | 60 | (oil)$^q$ |
| 21 | CH₃ | 3-Br | H | A | | |
| 22 | CH₃ | 4-Br | H | A | | |
| 23 | CH₃ | 2-Br | H | A | | |
| 24 | CH₃ | 2-Cl | H | A | | |
| 25 | CH₃ | 3-Cl | H | A | | |
| 26 | CH₃ | 4-Cl | H | A | | |
| 27 | CH₃ | 2-COφ | H | A,C | | |
| 28 | CH₃ | 3-COφ | H | A,C | | |
| 29 | CH₃ | 4-COφ | H | A,C | | |
| 30 | CH₃ | 2-SO₂CH₃ | H | A,C | | |
| 31 | CH₃ | 3-SO₂CH₃ | H | A,C | | |
| 32 | CH₃ | 4-SO₂CH₃ | H | A,C | | |
| 33 | CH₃ | 2-CO₂H | H | A,C | | |
| 34 | CH₃ | 2-CO₂CH₃ | H | A,C | | |
| 35 | CH₃ | 3-CO₂H | H | A,C | | |
| 36 | CH₃ | 3-CO₂CH₃ | H | A,C | | |
| 37 | CH₃ | 4-CO₂H | H | A,C | | |
| 38 | CH₃ | 4-CO₂CH₃ | H | A,C | | |
| 39 | CH₃ | 2-SO₂N(CH₃)₂ | H | C | | |
| 40 | CH₃ | 3-SO₂N(CH₃)₂ | H | C | | |
| 41 | CH₃ | 4-SO₂N(CH₃)₂ | H | C | | |
| 42 | CH₃ | 2-N(CH₃)₂ | H | C | | |
| 43 | CH₃ | 3-N(CH₃)₂ | H | C | | |
| 44 | CH₃ | 4-N(CH₃)₂ | H | C | | |

φ = phenyl
$^a$mass spec. m/z = 300
$^b$mass spec. m/z = 286
$^c$mass spec. m/z = 342
$^d$mass spec. m/z = 343
$^e$mass spec. m/z = 286
$^f$mass spec. m/z = 286
$^g$mass spec. m/z = 288
$^h$mass spec. m/z = 314
$^i$mass spec. m/z = 314
$^j$mass spec. m/z = 330
$^k$mass spec. m/z = 300
$^l$mass spec. m/z = 300
$^m$mass spec. m/z = 312
$^n$mass spec. m/z = 288
$^o$mass spec. m/z = 270
$^p$mass spec. m/z = 285
$^q$mass spec. m/z = 285

EXAMPLE 45

Part A: Trans-1-cyclohexyl-2-hydroxy-acenaphthane

To a solution of acenaphthene oxide (2.10 g, 0.0125 mole) in diethyl ether (80.0 ml) at 0° was added cyclohexylmagnesium chloride (12.0 ml of a 2M solution) dropwise. The reaction mixture was stirred at room temperature for one hour, quenched with saturated ammonium chloride and the crude product isolated by extraction with diethyl ether. Recrystallization (from n-butylchloride) afforded a white solid (1.50 g, 48%), m.p. 159°–160°.

Part B: 1-Cyclohexyl-1,2-Dihydro-2-propenoxy) Acenaphthene

To a solution of the product of Part A (1.50 g, 0.0006 mole) in tetrahydrofuran (15.0 ml) at 0° was added potassium t-butoxide (1.10 g, 0.010 mole). The mixture was stirred at 0° for 1 hour and cooled to −78°. To this solution was added allyl bromide (6.30 g, 0.052 mole) and the mixture was allowed to warm to room temperature over 24 hours. The mixture was quenched with water, and the crude product isolated by extraction with diethylether and chromatographed on silica to yield an oil (1.20 g, 74%); mass spec. m/z=292.

Part C: 3-(2-Cyclohexyl-1,2-dihydro-1-acenaphthenoxy)-1-propanol

To a solution of the product of Part B (6.50 g, 0.022 mole) in tetrahydrofuran (65.0 ml) was added borane (9.10 ml of 1.0M solution) at 0°. The reaction mixture was stirred for 1 hour at room temperature. The mixture was quenched slowly with $H_2O$ (2.60 ml), 3M NaOH (2.60 ml), and 30% hydrogen peroxide (13.0 ml) at 25°. The mixture was stirred for 1 hour and the crude product isolated by extraction with diethyl ether and chromatographed on silica with ethyl acetate/hexane to afford a white solid (3.70 g, 53%), m.p. 80°–82°.

Part D: 3-(2-Cyclohexyl-1,2-dihydro-1-acenaphthenoxy)-1-propanal

To a solution of the product of Part C (0.400 g, 0.0013 mole) in methylene chloride (20.0 ml) was added pyridinium chlorochromate (0.700 g, 0.0032 mole). The mixture was stirred for 3 hours at room temperature, quenched with diethyl ether (200.0 ml), and filtered through florisil and evaporated to an oil. Purification by chromatography with ethyl acetate/hexane afforded an oil (0.280 g, 70%), mass spec. m/z=308.

Part E: 3-(2-Cyclohexyl-1,2-dihydro-1-acenaphthenoxy)-1-methoximinopropane

To a solution of the product of Part D (0.250 g, 0.0008 mole) in pyridine (5.0 ml) and ethanol (5.0 ml) was added methoxylamine hydrochloride (0.075 g, 0.0009 mole) at room temperature. The mixture was refluxed for 24 hours and the solvents were removed in vacuo. The residue was taken up in diethyl ether and evaporated to an oil. Chromatography on silica with ethyl acetate/hexane afforded an oil (0.270 g, 38%).

Part F: 3-(1-Cyclohexyl-1,2-dihydro-1-acenaphthene-yl)propanamine hydrochloride To a solution of sodium borohydride (0.151 g, 0.004 mole) dissolved in tetrahydrofuran (8.0 ml) was added trifluoroacetic acid (0.460 g, 0.004 mole) dropwise at room temperature for 30 minutes. To this solution was added the product of Part E (0.270 g, 0.0008 mole) in tetrahydrofuran (3.0 ml) dropwise and the mixture was heated at reflux for 1 hour. The reaction mixture was quenched with water and evaporated in vacuo. The residue was extracted with methylene chloride and evaporated. The residue was diluted with ether and hydrochloric acid was bubbled through the solution. The precipitate was filtered to yield a white solid (0.185 g, 67%), m.p. 124°–126° dec.

The compound of Example 45 is shown in Table II, as well as other compounds which were prepared or could be prepared using the procedures of the aforementioned examples.

TABLE II

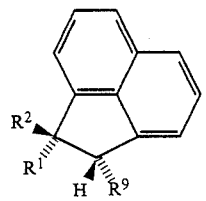

| EX. | $R^1$ | $R^2$ | $R^9$ | YIELD % | MP °C. |
|---|---|---|---|---|---|
| 45 | H | cyclohexyl | $O(CH_2)NH_2 \cdot HCl$ | 67 | 124–126 |
| 46 | H | $p\text{-}FC_6H_4CH_2$ | $O(CH_2)_2NH_2 \cdot HCl$ | 38 | hygroscopic |
| 47 | H | $CH_3(CH_2)_4CH_2$ | $O(CH_2)_3NH_2 \cdot HCl$ | | |
| 48 | H | $C_6H_5CH_2$ | $O(CH_2)_3NH_2 \cdot HCl$ | | |
| 49 | H | $C_6H_5$ | $O(CH_2)_3NH_2 \cdot HCl$ | | |
| 50 | H | $C_6H_5CH_2$ | $O(CH_2)_2OCH_3$ | | |
| 51 | H | $4\text{-}FC_6H_4CH_2$ | $O(CH_2)_2OCH_3$ | | |
| 52 | H | $2\text{-}CH_3OC_6H_4CH_2$ | $O(CH_2)_2OCH_3$ | | |
| 53 | H | $3\text{-}CH_3OC_6H_4CH_2$ | $O(CH_2)_2OCH_3$ | | |
| 54 | H | $4\text{-}CH_3OC_6H_4CH_2$ | $O(CH_2)_2OCH_3$ | | |
| 55 | H | $C_6H_5CH_2$ | $O(CH_2)_2OC(O)CH_3$ | | |
| 56 | H | $C_6H_5$ | $O(CH_2)_2OC(O)CH_3$ | | |
| 57 | H | $4\text{-}FC_6H_4CH_2$ | $O(CH_2)_2OC(O)CH_3$ | | |
| 58 | H | $2\text{-}CH_3OC_6H_4CH_2$ | $O(CH_2)_2OC(O)CH_3$ | | |
| 59 | H | $3\text{-}CH_3OC_6H_4CH_2$ | $O(CH_2)_2OC(O)CH_3$ | | |
| 60 | H | $CH_3(CH_2)_4CH_2$ | $O(CH_2)_3COCH_3$ | | |
| 61 | H | $C_6H_5CH_2$ | $O(CH_2)_3COCH_3$ | | |
| 62 | H | $C_6H_5$ | $O(CH_2)_3COCH_3$ | | |
| 63 | H | $4\text{-}FC_6H_4$ | $O(CH_2)_2COCH_3$ | | |
| 64 | H | $2\text{-}CH_3OC_6H_4CH_2$ | $O(CH_2)_2COCH_3$ | | |
| 65 | H | $4\text{-}CH_3OC_6H_4CH_2$ | $O(CH_2)_2COCH_3$ | | |
| 66 | H | $3\text{-}CH_3OC_6H_4CH_2$ | $O(CH_2)_2COCH_3$ | | |
| 67 | H | $C_6H_5$ | $O(CH_2)_3N(CH_3)_2$ | | |
| 68 | H | $4\text{-}FC_6H_4CH_2$ | $O(CH_2)_2N(CH_3)_2$ | | |
| 69 | H | $2\text{-}CH_3OC_6H_4CH_2$ | $O(CH_2)_2N(CH_3)_2$ | | |
| 70 | H | $3\text{-}CH_3OC_6H_4CH_2$ | $O(CH_2)_2N(CH_3)_2$ | | |
| 71 | H | $4\text{-}CH_3OC_6H_4CH_2$ | $O(CH_2)_2N(CH_3)_2$ | | |

Dosage and Dosage Forms

The phospholipase $A_2$ inhibitors of this invention can be administered to treat inflammatory and/or allergic conditions, including but not limited to rheumatoid arthritis and other rheumatic disorders, collagen diseases, dermatoses, allergic diseases, chronic obstructive and bronchospastic lung diseases such as asthma and bronchitis. The compounds of this invention may also be useful in the treatment of osteoarthritis.

They may be administered by any means that enables the active agent to reach the agent's site of action in the body of a mammal. They can be administered by any of the conventional means available for administration of pharmaceuticals, either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration generally contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler, or topically as an ointment, cream or lotion.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose) and related sugar solutions, and glycols such as propylene glycol or polyethylene glycols are suitable carriers for parenteral solutions. Solutions for parenteral administration contain the active ingredient, and, if necessary, suitable stabilizing agents, and/or buffer substances. Antioxidants such as sodium bisulfite, sodium sulfite, or ascorbic acid either alone or in combination are frequently suitable stabilizing agents. Also used are citric acid and its salts and sodium EDTA. In addition, parenteral solutions can contain preservatives, such as benzalkonium chloride, methyl and/or propyl parabens, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules each containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by dissolving 1.5% by weight of active ingredient in a solution containing 10% by volume of propylene glycol in water. The solution is sterilized by commonly used techniques.

Suspension

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Nasal Spray

An aqueous solution is prepared such that each 1 milliliter contains 10 milligrams of active ingredient, 1.8 milligrams methylparaben, 0.2 milligrams propylparaben and 10 milligrams methylcellulose. The solution is dispensed into 1 milliliter vials.

Lung Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

Topical Formulation

An ointment for topical administration may be prepared by adding the active ingredient to a mixture of 48% by weight white petrolatum, 10% liquid petrolatum, 8% glyceryl monostearate, 3% isopropyl myristate and 20% lanolin at 70° C. After thorough mixing, a warm solution of methyl and propyl parabens in water containing sodium acetone bisulfite is added such that the final concentration of each paraben is 0.15%, of water is 8% and of sodium acetone bisulfite is 0.5%. The mixture is stirred until it has reached room temperature.

Phospholipase A₂ Inhibition Test System

The compounds of this invention have been shown to inhibit phospholipase A₂ in an in vitro test system using the porcine pancreatic PLA₂ enzyme and an assay modified from Hirata et al. (*Proc. Natl. Acad. Sci* (USA), 77, 2533, 1980). The reaction was run in a total volume of 0.1 ml with the enzyme at a final concentration of 19 units/ml (0.025 μg protein/ml) which gave approximately 5000–8000 dpm (disintegration per minute) of activity in a buffer containing 25 mM Tris (trihydroxymethyl aminoethane), 25 mM glycylglycine, 25 mM CaCl₂ and 0.75 mM EDTA (tetra sodium salt), pH 8.5. The drug was added to the enzyme solution, incubated for 2 minutes, and the substrate, [arachidonyl-1-¹⁴C]L-α-1-palmitoyl-2-arachidonyl phosphatidylcholine, at a final concentration of 7 μM (40,000 dpm), was then added to begin the reaction which proceeded for five minutes at 37° C. The reaction was stopped by freezing in a dry ice-ethanol slurry and the arachidonic acid product was separated from the unreacted substrate using silica gel columns.

All reactions were run in duplicate. Inhibitors were made up in 0.2M Tris-Cl (trihydroxymethyl aminoethane hydrochloride), pH 8.5 or dissolved in DMSO and then diluted with Tris-Cl buffer (maximum DMSO concentration, 7%). The IC₅₀ was determined by inspection of a semilog plot of % inhibition versus final inhibitor concentration.

The enzyme phospholipase A₂ (PLA₂), catalyzes the release of fatty acids from the 2-position of phospholipids, particularly phosphatidyl choline. Arachidonic acid (AA) is most frequently found at the 2-position of phospholipids. Once it is released by the action of PLA₂, AA can be oxygenated by cyclooxygenase and lipoxygenases to the potent inflammatory mediators prostaglandins and leukotrienes, respectively. Inhibition of PLA₂ will block the generation of these local inflammatory mediators, thereby reducing inflammation. Since AA is the substrate for both cyclooxygenases and lipoxygenases, inhibition of PLA₂ will reduce the levels of both prostaglandins and leukotrienes. Many current anti-inflammatory drugs, e.g., salicylates, inhibit cyclooxygenases but not lipoxygenases, so that only prostaglandin levels are reduced.

"Consisting essentially of" in the present disclosure is intended to have its customary meaning; namely, that all specified material and conditions are very important in practicing the invention but that unspecified materials and conditions are not excluded so long as they do not prevent the benefits of the invention from being realized.

What is claimed is:

1. A pharmaceutical composition, consisting essentially of: (i) a substituted acenaphthene phospholipase A₂ inhibitor having the formula:

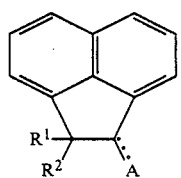

wherein $R^1$ is H or $C_1$–$C_3$ alkyl;

$R^2$ is $C_3$–$C_{10}$ alkyl, $C_4$–$C_{10}$ cycloalkyl, or aryl($CH_2)_n$—; and $R^1$ and $R^2$, taken together, may be aryl—CH= where n=1–4, and aryl is

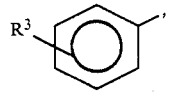

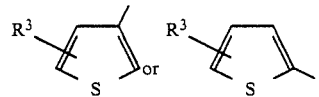

$R^3$ is H, CN, NO₂, CO—phenyl, S(O)$_e$R⁵, halogen, NHCOR⁴, CO₂R⁴, OR⁴, SO₂N(R⁴)₂, or NR⁶R⁷, wherein e=0, 1 or 2;

$R^4$ is H, $C_1$–$C_6$ alkyl, or phenyl;

$R^5$ is $C_1$–$C_6$ alkyl, phenyl;

$R^6$ and $R^7$, independently are H or $C_1$–$C_4$ alkyl;

and wherein

A is =O, =CHR⁸,

=NOR⁸

$R^8$ is H, $C_1$–$C_6$ alkyl, or $(CH_2)_mW$;

$R^9$ is $C_1$–$C_6$ alkyl, $(CH_2)_mW$, or —X$(CH_2)_mW$;

where m=1–6, X is O, S,

W is —OR¹⁰, —COR¹⁰, —OCOR¹⁰, —OCOOR¹⁰, NR¹¹R¹², or CONR¹¹R¹²;

$R^{10}$ is $C_1$–$C_6$ alkyl;

$R^{11}$, $R^{12}$, independently are H, $C_1$–$C_6$ alkyl;

provided that:

1. When A=O then R¹ and R² taken together are not 4—(CH₃)₂NC₆H₄CH=, 2—MeOC₆H₄CH=3—MeOC₆H₄CH=, 4—FC₆H₄CH=, or 4—MeOC₆H₄CH=;
2. When A is =NOR₈, R₈ is not H;
3. When R⁸ is hydrogen, then R² is not $C_3$–$C_{10}$ alkyl or $C_4$–$C_{10}$ cycloalkyl;
4. When R² is 4—FC₆H₄CH₂—, 3—CH₃CONHC₆H₄CH₂—, or 4—NO₂C₆H₄CH₂—, then A is not =CH₂;
5. When A=O, then R² is not $C_3$–$C_{10}$ alkyl or $C_4$–$C_{10}$ cycloalkyl;
6. When A is CH₂NR¹¹R¹², then R² is not alkyl;

in an amount sufficient to provide anti-inflammatory and/or anti-allergic effects in a mammal suffering from a phospholipase A₂-mediated condition, and (ii) a pharmaceutically acceptable carrier.

2. A pharmaceutical composition according to claim 1, wherein A is =O, =CHR⁸ or

3. A pharmaceutical composition according to claim 1, wherein W is —NR¹¹R¹² or —CONR¹¹R¹².

4. A pharmaceutical composition according to claim 1, wherein R¹ is H or CH₃.

5. A pharmaceutical composition according to claim 1, wherein $R^2$ is aryl$(CH_2)_n$— and n=1-2.

6. A pharmaceutical composition according to claim 1, wherein $R^1$ and $R^2$, taken together, are aryl—CH=.

7. A pharmaceutical composition according to claim 1, wherein $R^3$ is halogen, CN, —$OCH_3$, —$OR^4$, or —$NR^6R^7$.

8. A pharmaceutical composition according to claim 1, wherein A is =O, =$CHR^8$, or

(provided that if A is

then $R^9$ is trans to $R^2$), where m=1-3.

9. A pharmaceutical composition according to claim 1, wherein W is $NR^{11}R^{12}$ or $COR^{11}R^{12}$.

10. A pharmaceutical composition according to claim 1, wherein the substituted acenaphthene phospholipase $A_2$ inhibitor is 1,2-Dihydro-1-[(3-methoxyphenyl)methyl)]-1-methyl-2-methylene acenaphthene.

11. A pharmaceutical composition according to claim 1, wherein the substituted acenaphthene phospholipase $A_2$ inhibitor is 3-[1,2-Dihydro-1-methyl-2-methylene-1-acenaphthenyl)-methyl]phenol.

12. A pharmaceutical composition according to claim 1, wherein the substituted acenaphthene phospholipase $A_2$ inhibitor is 3-(1,2-Dihydro-2-[(3-methoxyphenyl)methyl]-2-methyl-1-acenaphthenylidine)propanamine.

13. A pharmaceutical composition according to claim 1, wherein the substituted acenaphthene phospholipase $A_2$ inhibitor is 2-[(3-Fluorophenyl)methylene]-1(2H)-acenaphthylenone.

14. A pharmaceutical composition according to claim 1, wherein the substituted acenaphthene phospholipase $A_2$ inhibitor is 1,2-Dihydro-1-[(3-cyanophenyl)methyl)]-1-methyl-2-methylene acenaphthene.

15. A method of treating inflammatory and/or allergic conditions mediated by phospholipase $A_2$ in a mammal, comprising administering to the mammal a therapeutically effective amount of a substituted acenaphthene compound having the formula:

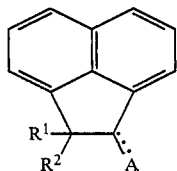

wherein
$R^1$ is H or $C_1$-$C_3$ alkyl;
$R^2$ is $C_3$-$C_{10}$ alkyl, $C_4$-$C_{10}$ cycloalkyl, or aryl($CH_2)_n$—; and
$R^1$ and $R^2$, taken together, may be aryl—CH= where n=1-4, and
aryl is

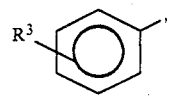

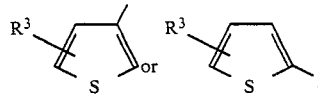

or $NHCOR^4$, $CO_2R^4$, $OR^4$, $SO_2N(R^4)_2$,
$R^3$ is H, CN, $NO_2$, CO—phenyl, $S(O)_eR^5$, halogen, $NR^6R^7$, wherein e=0, 1 or 2;
$R^4$ is H, $C_1$-$C_6$ alkyl, or phenyl;
$R^5$ is $C_1$-$C_6$ alkyl, phenyl;
$R^6$ and $R^7$, independently are H or $C_1$-$C_4$ alkyl;
and wherein
A is =O, =$CHR^8$,

=$NOR^8$
$R^8$ is H, $C_1$-$C_6$ alkyl, or $(CH_2)_mW$;
$R^9$ is $C_1$-$C_6$ alkyl, $(CH_2)_mW$, or —$X(CH_2)_mW$;
where m=1-6, X is O, S,
W is —$OR^{10}$, —$COR^{10}$, —$OCOR^{10}$, —$OCOOR^{10}$, $NR^{11}R^{12}$, or $CONR^{11}R^{12}$;
$R^{10}$ is $C_1$-$C_6$ alkyl;
$R^{11}$, $R^{12}$, independently are H, $C_1$-$C_6$ alkyl;
provided that:
1. When A=0 then $R^1$ and $R^2$ taken together are not 4—$(CH_3)_2NC_6H_4CH$=, 2—$MeOC_6H_4CH$=, 3—$MeOC_6H_4CH$=, 4—$FC_6H_4CH$=, or 4—$MeOC_6H_4CH$=;
2. When A is =$NOR_8$, $R_8$ is not H;
3. When $R^8$ is hydrogen, then $R^2$ is not $C_3$-$C_{10}$ alkyl or $C_4$-$C_{10}$ cycloalkyl;
4. When $R^2$ is 4—$FC_6H_4CH_2$—, 3—$CH_3CONHC_6H_4CH_2$—, or 4—$NO_2C_6H_4CH_2$—, then A is not =$CH_2$;
5. When A=0, then $R^2$ is not $C_3$-$C_{10}$ alkyl or $C_4$-$C_{10}$ cycloalkyl;
6. When A is $CH_2NR^{11}R^{12}$, then $R^2$ is not alkyl.

16. A method of treating inflammatory and/or allergic conditions mediated by phospholipase $A_2$ in a mammal, comprising administering to the mammal a therapeutically effective amount of the substituted acenaphthene compound set forth in claim 10.

17. A method of treating inflammatory and/or allergic conditions mediated by phospholipase $A_2$ in a mammal, comprising administering to the mammal a therapeutically effective amount of the substituted acenaphthene compound set forth in claim 11.

18. A method of treating inflammatory and/or allergic conditions mediated by phospholipase $A_2$ in a mammal, comprising administering to the mammal a therapeutically effective amount of the substituted acenaphthene compound set forth in claim 12.

19. A method of treating inflammatory and/or allergic conditions mediated by phospholipase $A_2$ in a mammal, comprising administering to the mammal a therapeutically effective amount of the substituted acenaphthene compound set forth in claim 13.

20. A method of treating inflammatory and/or allergic conditions mediated by phospholipase $A_2$ in a mammal, comprising administering to the mammal a therapeutically effective amount of the substituted acenaphthene compound set forth in claim 14.

* * * * *